(12) United States Patent
Schlitt et al.

(10) Patent No.: US 8,004,170 B2
(45) Date of Patent: Aug. 23, 2011

(54) TANNING LAMP

(76) Inventors: Steven C. Schlitt, Merrimac, MA (US);
Pascal Horion, Drummondville (CA);
Alain Richer, Drummondville (CA)

( * ) Notice: Subject to any disclaimer, the term of this patent is extended or adjusted under 35 U.S.C. 154(b) by 235 days.

(21) Appl. No.: 12/231,011

(22) Filed: Aug. 28, 2008

(65) Prior Publication Data

US 2010/0052505 A1    Mar. 4, 2010

(51) Int. Cl.
*H01J 17/16* (2006.01)

(52) U.S. Cl. .................... 313/486; 313/635; 313/634

(58) Field of Classification Search .................. None
See application file for complete search history.

(56) References Cited

U.S. PATENT DOCUMENTS

| | | | |
|---|---|---|---|
| 3,717,781 A | 2/1973 | Sadoski et al. | 313/109 |
| 3,987,331 A | 10/1976 | Schreurs | 313/486 |
| 3,988,633 A | 10/1976 | Shurgan et al. | 313/493 |
| 4,703,184 A | 10/1987 | Wolff | 250/504 R |
| 4,825,125 A | 4/1989 | Lagushenko et al. | 313/493 |
| 4,924,141 A | 5/1990 | Taubner et al. | 313/488 |
| 5,557,112 A | 9/1996 | Csoknyai et al. | 250/504 R |
| 5,565,685 A | 10/1996 | Czako et al. | 250/504 R |
| 6,777,702 B2 | 8/2004 | Laudano et al. | 250/504 R |
| 6,943,361 B2 | 9/2005 | Laudano et al. | 250/504 R |
| 7,259,382 B2 | 8/2007 | Laudano et al. | 250/504 R |
| 2005/0261751 A1* | 11/2005 | Justel et al. | 607/88 |

* cited by examiner

*Primary Examiner* — Anne Hines
*Assistant Examiner* — Tracie Green

(57) ABSTRACT

A low pressure fluorescent tanning lamp (10) includes an elongated, tubular glass envelope (12) including an arc generating and sustaining medium (14) and electrodes (16) therewithin and having a first section (18) and a second section (20). A phosphor coating (22) is provided on the interior of the first section (18) and only a portion (24) of the second section (20). The phosphor coating comprises materials emitting in the UVA and UVB areas of the electromagnetic spectrum and additionally in the visible area of the electromagnetic spectrum in the range above 600 nm. The second section (20) includes a clear window (26) and the phosphor comprises a mixture comprising about 91% $BaSi_2O_5:Pb$; about 6% $MgSrAl_{10}O_{17}:Ce$; and about 3% $Y_2O_3:Eu$.

9 Claims, 2 Drawing Sheets

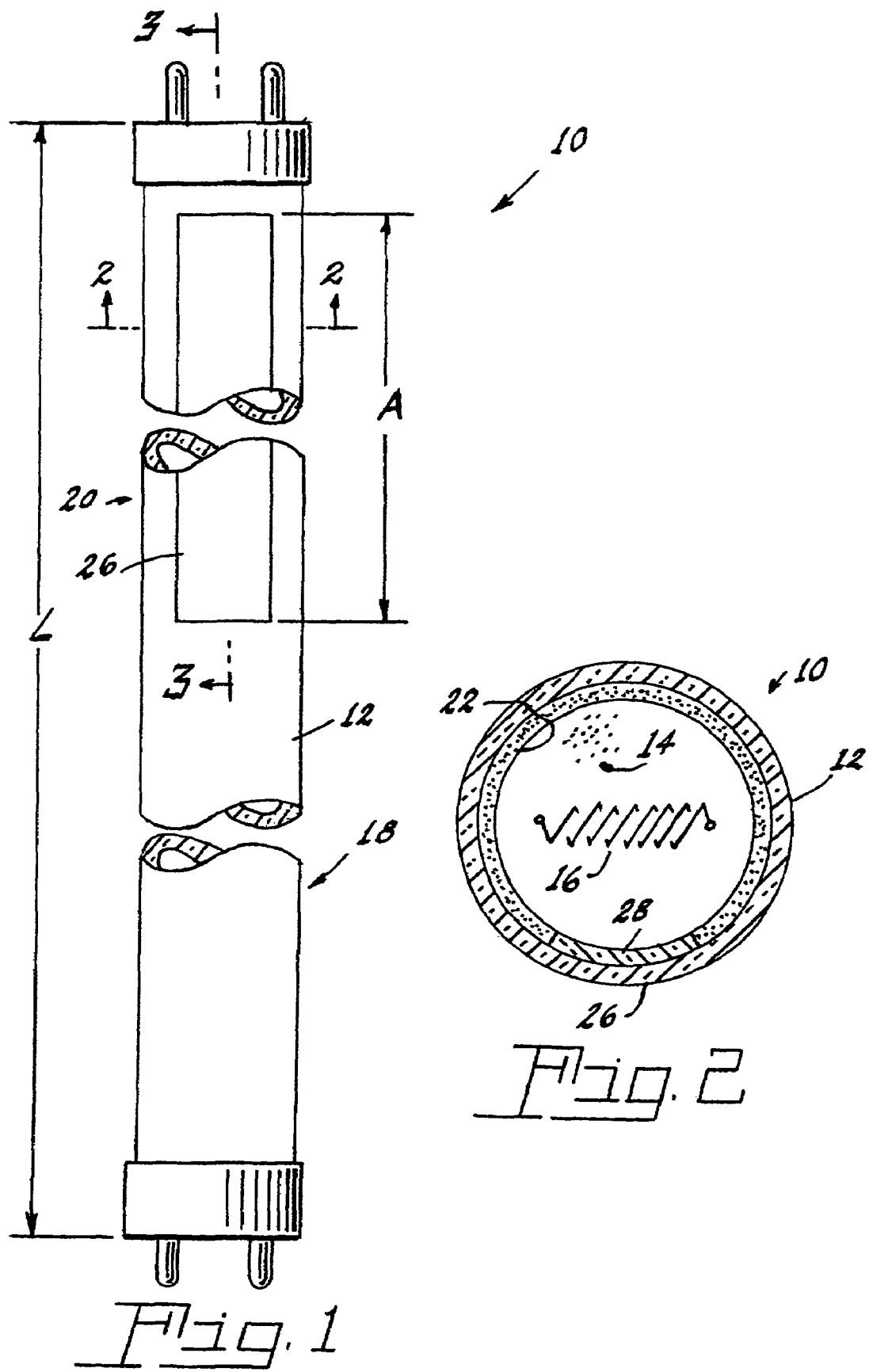

TANNING LAMP

TECHNICAL FIELD

This invention relates to fluorescent lamps and more particularly to fluorescent lamps employed for indoor tanning.

BACKGROUND ART

Tanning lamps are known commodities and have been employed for some time in tanning booths and tanning beds. It has been a problem to provide even tanning where the facial features are concerned because of the higher levels of melanin pigments in the face, resulting from more frequent exposure to the sun than the rest of the body. Prior attempts at correcting this problem have used additional lamps in the face area; high pressure UV lamps; lamps with multiple areas of differing phosphors to provided differing radiation zones; and lamps with specialized grooves formed in the head-end of the lamp.

These processes have been complicated and expensive. Thus, there is a continuing need for discharge lamps for use in tanning facilities that provide enhanced performance.

DISCLOSURE OF INVENTION

It is, therefore, an object of the invention to obviate the disadvantages of the prior art.

It is another object of the invention to improve tanning lamps.

It is another object of the invention to enhance the tanning operation.

These objects are accomplished, in one aspect of the invention, by the provision of a low pressure fluorescent tanning lamp comprising: an elongated, tubular glass envelope including an arc generating and sustaining medium therewithin and having a first section and a second section; a phosphor coating on the interior of said first section and a phosphor coating on only a portion of said second section, said phosphor coating comprising materials emitting in the UVA and UVB areas of the electromagnetic spectrum and additionally in the visible area of the electromagnetic spectrum in the range above 600 nm. In a preferred embodiment of the invention the second section includes a clear window.

This lamp provides clear advantages over those of the prior art. It is simple to manufacture, utilizing only techniques that have long been used in the making of conventional fluorescent lamps. The application of the clear window allows increased radiation in a desired area by employing conventional envelopes without the necessity of additional glass forming. Further, it eliminates the need for additional high pressure lamps.

BRIEF DESCRIPTION OF THE DRAWINGS

FIG. 1 is an elevation view of an embodiment of the invention;

FIG. 2 is a sectional view taken along the line 2-2 of FIG. 1; and

BEST MODE FOR CARRYING OUT THE INVENTION

Figure 3:
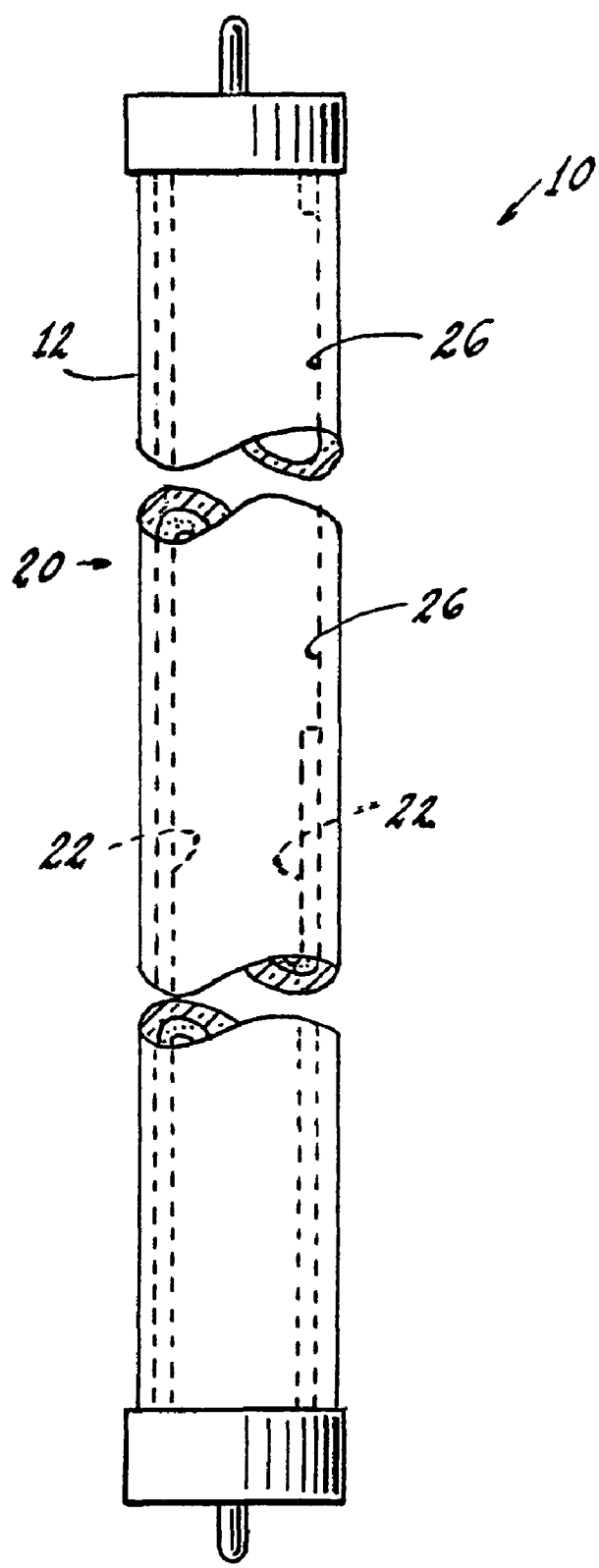
FIG. 3 is a sectional view taken along the line 3-3 of FIG. 1.

For a better understanding of the present invention, together with other and further objects, advantages and capabilities thereof, reference is made to the following disclosure and appended claims taken in conjunction with the above-described drawings.

Referring now to the drawings with greater particularity, there is shown in FIGS. 1 and 2 a low-pressure fluorescent lamp 10 that includes an elongated, tubular glass envelope 12 including an arc generating and sustaining medium 14 and having electrodes 16 (only one of which is shown) therewithin and having a first section 18 and a second section 20. The glass envelope is preferably a soda-lime glass having a transmission of 65% at 313 nm with no more than a 2.5% transmission at 280 nm. A phosphor coating 22 is provided on the interior of the first section 18 and on only a portion 24 of the second section 20. The phosphor coating comprises materials emitting in the UVA and UVB areas of the electromagnetic spectrum and additionally in the visible area of the electromagnetic spectrum in the range above 600 nm for reasons that will be explained below. Because the phosphor coating 22 exists only on a portion of the second section 20 a clear window 26 is provided (see FIG. 3).

In a preferred embodiment of the invention the phosphor coating 22 comprises a mixture of about 91% $BaSi_2O_5{:}Pb$ (which emits in the UVA region of the spectrum; i.e., 320-400 nm); about 6% $MgSrAl_{10}O_{17}{:}Ce$ (which emits in the UVB region of the spectrum; i.e., 260-320 nm); and about 3% $Y_2O_3{:}Eu$ (which emits in the visible, red region of the spectrum, preferably above 600 nm).

The clear window 26 extends about 30° to 45° of the circumference of said envelope 12, which is preferably a T12 diameter (1 and ½ inches).

The low pressure fluorescent lamp 10 has a given length L which preferably is from about 72 to about 80 inches and the clear window 26 extends from one end of said lamp for a distance A which is less than L and preferably is about ¼ of the given length L, i.e., about 18 to 20 inches.

In a preferred embodiment, a lamp employing the phosphors described above has a buffer gas of argon at a pressure of between 2.0 and 2.5 Torr and sufficient mercury to ensure good operation. The length is the afore-mentioned 72 to 80 inches. The clear window 26 is formed by removing a like portion of the phosphor coating and extends a width of ~0.5 to 0.6 inches about the circumference, which exposes to view the phosphor-coated surface opposite the window. Since the clear window 26 would be subject to solarization from the UVC radiation generated by the discharge and would be vulnerable to chemical reactions between the mercury and sodium contained in the glass envelope 12, it is preferable to protect this clear area 26 with a metal oxide coating 28, such as an aluminum oxide coating about 0.8 to 1.2 $mg/cm^2$ thick.

The clear window 26 opens a view to the mercury gas discharge during lamp operation and it is this open view of the discharge combined with the transmission characteristics of the glass envelope 12 that allows this second section 20 of the lamp to exhibit higher UVB radiance than the first section 18.

The addition of the visible light emitting phosphor to the predominantly UV phosphor blend imparts a reddish/pink coloration to the emission throughout the general body of the lamp 10. The clear window 26, because it gives visual access to the arc discharge, has a contrasting bluish-white appearance arising from the fact that the Hg—Ar arc exhibits radiance in the blue region of the spectrum.

Thus, there is provided an enhanced fluorescent tanning lamp that provides additional radiation for the facial features and additionally provides an improved appearance.

While there have been shown and described what are at present considered to be the preferred embodiments of the invention, it will be apparent to those skilled in the art that various changes and modifications can be made herein without departing from the scope of the invention as defined by the appended claims.

What is claimed is:

1. A low pressure fluorescent tanning lamp comprising:
   an elongated, tubular glass envelope including an arc generating and sustaining medium therewithin and having a first section and a second section;
   a phosphor coating on the interior of said first section and a phosphor coating on only a portion of said second section, said phosphor coating comprising materials emitting in the UVA and UVB areas of the electromagnetic spectrum and additionally in the visible area of the electromagnetic spectrum in the range above 600 nm;
   wherein said second section includes a clear window in only a portion thereof.

2. A low pressure fluorescent tanning lamp comprising:
   an elongated, tubular glass envelope including an arc generating and sustaining medium therewithin and having a first section and a second section;
   a phosphor coating on the interior of said first section and a phosphor coating on only a portion of said second section, said phosphor coating comprising materials emitting in the UVA and UVB areas of the electromagnetic spectrum and additionally in the visible area of the electromagnetic spectrum in the range above 600 nm;
   wherein said second section includes a clear window; and
   wherein said phosphor coating comprises about 91% $BaSi_2O_5$:Pb; about 6% $MgSrAl_{10}O_{17}$:Ce; and about 3% $Y_2O_3$:Eu.

3. The low pressure fluorescent lamp of claim 2 wherein said clear window extends about 30° to 45° of the circumference of said envelope.

4. The low pressure fluorescent lamp of claim 2 wherein said lamp has a given length L and said clear window extends from one end of said lamp for a distance A which is less than L.

5. The low pressure fluorescent lamp of claim 4 wherein said distance A is about ¼ of said given length L.

6. The low pressure fluorescent lamp of claim 2 wherein said clear window is covered by an optically transparent metal oxide coating.

7. The low pressure fluorescent lamp of claim 1 wherein said clear window extends from about 30° to 45° of the circumference of said envelope.

8. The low pressure fluorescent lamp of claim 7 wherein the length of the lamp is from about 72 to about 80 inches and the clear window extends from one end of said lamp for a distance of from about 18 to 20 inches.

9. The low pressure fluorescent lamp of claim 7 wherein said clear window is covered by an optically transparent metal oxide coating.

* * * * *